United States Patent [19]

Banitt

[11] Patent Number: 4,952,574

[45] Date of Patent: Aug. 28, 1990

[54] ANTIARRHYTHMIC SUBSTITUTED N-(2-PIPERIDYLMETHYL)BENZAMIDES

[75] Inventor: Elden H. Banitt, Woodbury, Minn.

[73] Assignee: Riker Laboratories, Inc., St. Paul, Minn.

[21] Appl. No.: 248,814

[22] Filed: Sep. 26, 1988

[51] Int. Cl.$^5$ .................. C07D 211/30; C07D 401/00
[52] U.S. Cl. ..................... 514/315; 514/316;
514/328; 546/233; 546/234; 546/244; 546/189;
546/208
[58] Field of Search ............... 546/233, 234, 244, 189,
546/208; 514/315, 316, 328

[56] References Cited

U.S. PATENT DOCUMENTS

| | | | |
|---|---|---|---|
| 3,342,826 | 9/1967 | Miller et al. | 546/233 |
| 3,900,481 | 8/1975 | Banitt et al. | 546/224 |
| 4,071,524 | 1/1978 | Banitt | 544/80 |
| 4,097,481 | 6/1978 | Banitt et al. | 546/234 |
| 4,339,587 | 7/1982 | Banitt | 260/544 |
| 4,452,983 | 6/1984 | Johnson et al. | 546/233 |
| 4,558,573 | 11/1985 | Bronn | 546/233 |
| 4,599,434 | 7/1986 | Banitt | 549/342 |
| 4,650,873 | 3/1987 | Leir | 546/233 |
| 4,656,285 | 4/1987 | Bronn | 546/291 |

OTHER PUBLICATIONS

J. Med. Chem. 1977, 20, 821 (Banitt, et al.).

*Primary Examiner*—John M. Ford
*Assistant Examiner*—Catherine Scalzo
*Attorney, Agent, or Firm*—Donald M. Sell; Walter N. Kirn; Robert W. Sprague

[57] ABSTRACT

Certain 2,5-disubstituted N-(2-piperidylmethyl)benzamides, wherein one substituent is 2,2,2-trifluoroethoxy, and pharmaceutically acceptable acid-addition salts thereof, are active as antiarrhythmic agents.

23 Claims, No Drawings

ANTIARRHYTHMIC SUBSTITUTED N-(2-PIPERIDYLMETHYL)BENZAMIDES

BACKGROUND OF THE INVENTION

Field of the Invention

The invention relates to substituted N-(2-piperidylmethyl)benzamides which are pharmaceutically active. More specifically, the invention relates to such compounds which exhibit antiarrhythmic activity. Pharmaceutical compositions comprising and pharmacological methods for using such compounds are also described.

Description of the Related Art

Certain substituted N-(2-piperidylmethyl) benzamides are known antiarrhythmic agents. Notable among these are the various mono-, bis- and tris-(2,2,2-trifluoroethoxy)-N-(2-piperidylmethyl)benzamides most notably the compound 2,5-bis(2,2,2-trifluoroethoxy)-N-(2-piperidylmethyl)benzamide acetate, which is an antiarrhythmic drug sold under the trade designation Tambocor ® brand flecainide acetate, disclosed in U.S. Pat. No. 3,900,481. Related to these compounds are the tertiary benzamides disclosed in U.S. Pat. No. 4,097,481 which also exhibit antiarrhythmic activity.

Disclosed in U.S. Pat. No. 4,339,587 is the antiarrhythmic compound 5-hydroxy-N-(2-piperidylmethyl)-2-(2,2,2-trifluoroethoxy)benzamide. Also disclosed is 5-hydroxy-N-(2-pyridylmethyl)-2-(2,2,2-trifluoroethoxy)benzamide, a precursor to the above-mentioned piperidyl analog and an intermediate in a synthesis of flecainide disclosed in U.S. Pat. No. 3,900,481. This compound also serves as an intermediate in the preparation of some of the compounds of the present invention.

Last, many of the compounds disclosed in the patents mentioned above are also disclosed in J. Med. Chem. 1977, 20, 821. Also described therein are several 2-(2,2,2-trifluoroethoxy)-N-(2-piperidylmethyl)benzamides in which the aryl ring is substituted in the 5-position by methyl, chloro, or fluoro. These latter compounds are said to possess substantially reduced antiarrhythmic activity as compared to the corresponding 5-(2,2,2-trifluoroethoxy) compound.

DETAILED DESCRIPTION OF THE INVENTION

The invention provides novel antiarrhythmic compounds of Formula I

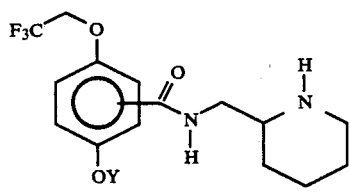

wherein Y is:
a straight chain or branched chain alkylene carboxylic acid of 2 to about 6 carbons, or a derivative thereof selected from the group consisting of primary amides, secondary lower alkyl amides, secondary phenyl(lower)alkyl amides, tertiary amides wherein the substituents form a five- or six-membered saturated ring, tertiary amides wherein the amide substituents are independently lower alkyl, tertiary amides wherein one amide substituent is lower alkyl and the other is phenyl (lower)alkyl, and lower alkyl esters; or straight chain or branched chain hydroxyalkyl of 2 to about 6 carbon atoms, or phenyl ether or lower alkyl ether derivatives thereof; or ω-phenylalkyl wherein the alkyl group contains one to about three carbon atoms; or straight chain or branched chain alkenyl of three to about six carbon atoms wherein the olefinic unsaturation does not render the phenolic oxygen vinylic; or straight chain or branched chain phenylalkenyl wherein the alkenyl group contains three to about six carbon atoms and wherein the olefinic unsaturation does not render the phenolic oxygen vinylic; or straight chain or branched chain alkyl of 1 to about 6 carbon atoms or a pharmaceutically acceptable acid-addition salt thereof.

Pharmaceutical compositions containing a compound of Formula I, and pharmacological methods for using a compound of Formula I as an antiarrhythmic agent are also described.

For the purposes of the instant specification and claims, the term "lower alkyl" is meant to include straight chain or branched chain alkyl groups of one to about four carbon atoms.

The synthetic route to the compounds of the invention is determined by the orientation of the substituent OY with respect to the benzamide carbonyl substituent and by the nature of Y, in that Y must be tolerant of subsequent reactions in the sequence. When the substituent Y is tolerant of conditions sufficient to reduce a pyridine ring (for example, various conventional hydrogenation conditions) compounds of the invention may be prepared by a route in which the piperidine ring is introduced via hydrogenation subsequent to the introduction of the group Y.

Accordingly, Scheme I below is drawn to preparation of compounds of Formula Ia, wherein OY of Formula I is ortho to the benzamide carbonyl substituent, and wherein Y is a derivative of a straight chain or branched chain alkylene carboxylic acid of 2

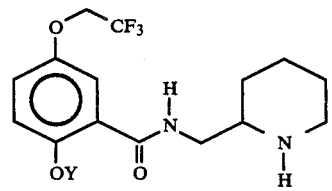

to about 6 carbon atoms selected from the group consisting of primary amides, secondary lower alkyl amides, secondary phenyl (lower) alkyl amides such that the amide nitrogen is not benzylic, tertiary amides wherein one of the amide substituents is lower alkyl and the other is phenyl(lower) alkyl such that the amide nitrogen is not benzylic, tertiary amides in which the substituents form a five- or six-membered saturated ring, and lower alkyl esters; straight chain or branched chain hydroxyalkyl of two to about six carbon atoms, or phenyl ether or lower alkyl ether derivatives thereof; or straight chain or branched chain alkyl of 1 to about 6 carbon atoms.

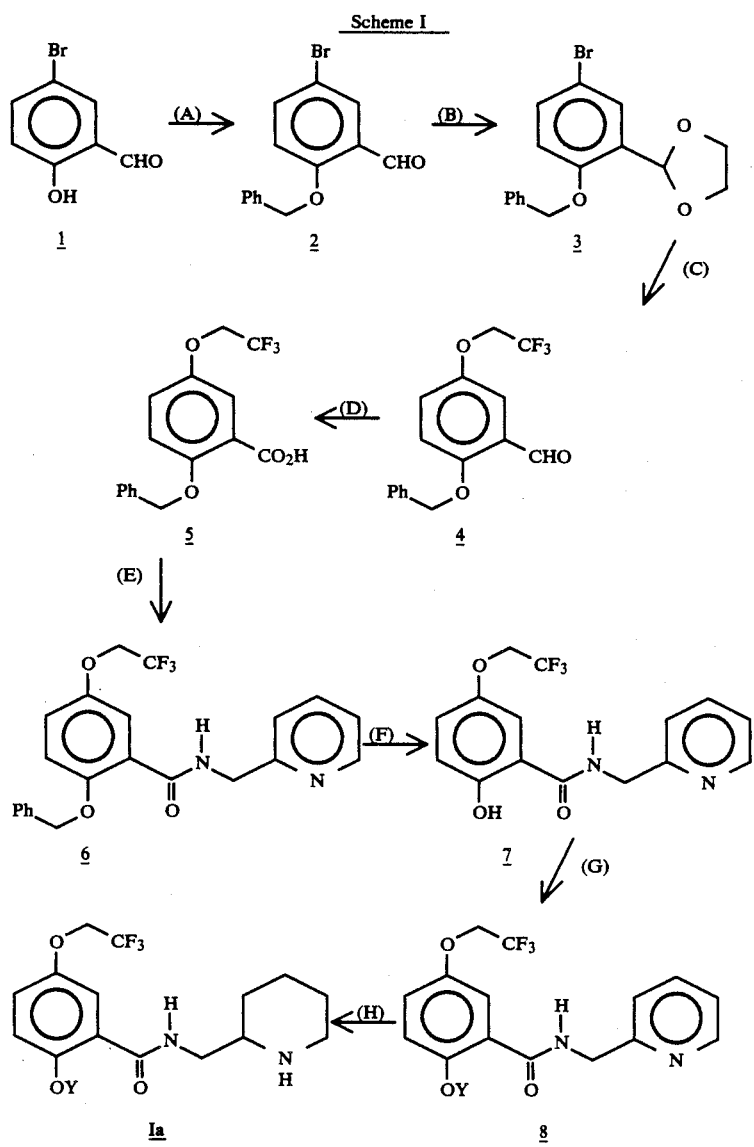

Shown in Scheme I is the synthetic route to key intermediate compound 7, from which many compounds of the invention may be prepared. In step (A), known 5-bromosalicylaldehyde 1 is benzylated by known methods, for example by treatment with a benzyl halide, preferably benzyl chloride, in a polar aprotic solvent such as dimethoxyethane, preferably (in the case of benzyl chloride) in the presence of sodium iodide and a buffering base such as potassium carbonate. The resulting benzylated compound 2 is further protected in step (B) by conversion to the ethylene acetal 3. Compound 3 is then alkylated in step (C) by treatment with sodium 2,2,2-trifluoroethoxide in a polar solvent comprising 2,2,2-trifluoroethanol in the presence of cuprous or cupric ion. Subsequent acid catalysed hydrolysis of the acetal affords aldehyde 4.

In step (D) of Scheme I, aldehyde 4 is oxidized to the corresponding carboxylic acid 5. While several oxidation methods may be adequate for this transformation, it is preferred that aldehyde 4 be first treated with hydroxylamine to form the aldoxime. The aldoxime is then dehydrated, preferably by acetic anhydride, to the corresponding nitrile. Hydrolysis of the nitrile then affords the acid 5.

Carboxylic acid 5 in step (E) is first converted to the corresponding acyl chloride by treatment with a reagent such as phosphorous pentachloride, oxalyl chloride, thionyl chloride, phosgene or the like. The resulting acyl chloride is then employed to acylate 2-aminomethylpyridine to form compound 6. Selective hydrogenolysis of the benzyl protecting group in compound 6, preferably with palladium on carbon catalyst, provides the key intermediate 7.

Compound 7 is then converted via steps (G) and (H) to a compound of Formula Ia. Step (G) involves reaction of compound 7 under conventional conditions with an appropriate electrophile which consists of a leaving group and the requisite group Y. Preferred conditions for this transformation when the leaving group is bromide involve treatment of compound 7 with a non-nucleophilic base such as sodium hydride, followed by addition of the appropriate electrophile. When the leaving group is chloride, addition of sodium iodide to the reaction mixture prior to addition of the electrophile facilitates the reaction.

The product of step (G), a compound of formula 8, is then reduced under conventional conditions to which the group Y is tolerant, preferably by hydrogenation with platinum oxide catalyst, to afford a compound of Formula Ia.

As an alternative to Scheme I, compounds of Formula Ia may be prepared according to Scheme II below:

the compound of formula 13 is hydrolyzed, converted to an acyl halide and reacted with 2-aminomethylpyridine to afford a compound of formula 8, which is then reduced as described in the above discussion of Scheme I to afford a compound of Formula Ia.

Similarly, compounds of Formula Ib, wherein OY of Formula I is meta to the amide carbonyl substituent, and wherein Y is as described for compounds of Formula Ia, are prepared from 5-hydroxy-N-(2-pyridylmethyl)-2-(2,2,2-trifluoroethoxy) benzamide 20 as shown

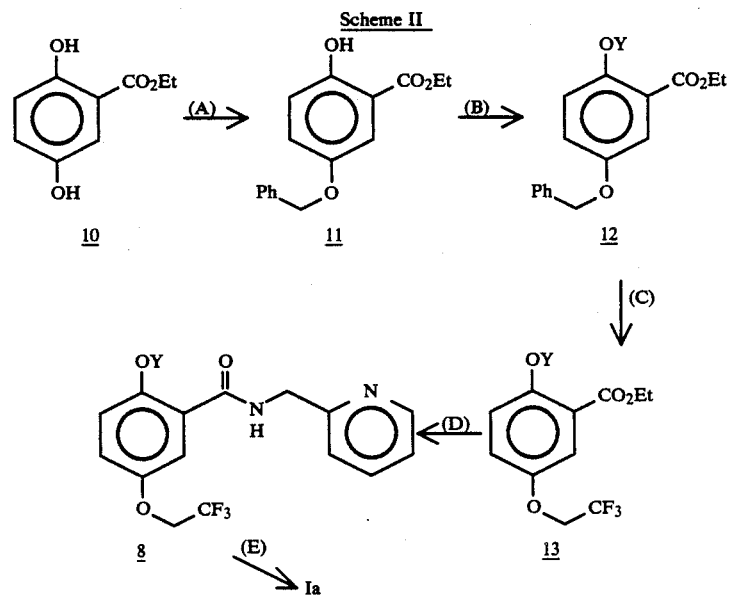

Step (A) of Scheme II involves selective benzylation in Scheme III below.

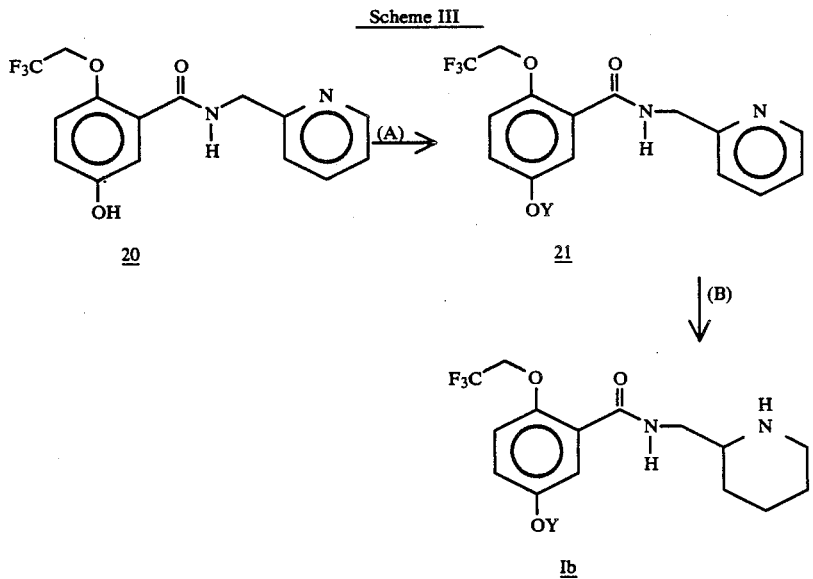

of the 5-hydroxyl group of known ethyl 2,5-dihydroxybenzoate 10 to afford compound 11. Step (B) is alkylation of the remaining phenolic oxygen as described in the above discussion of Scheme I to provide a compound of formula 12. Step (C) involves (1) hydrogenolysis of the benzyl moiety and (2) reacting the resulting phenol with 2,2,2-trifluoroethyl trifluoromethanesulfonate to provide a compound of formula 13. In Step (D), Compound 20 and a method of preparation therefor are disclosed in U.S. Pat. No. 4,399,587 which is incorporated herein by reference. Steps (A) and (B) of Scheme III correspond to Steps (G) and (H) of Scheme I.

In the alternative, compounds of Formula Ib may be prepared according to Scheme IV below:

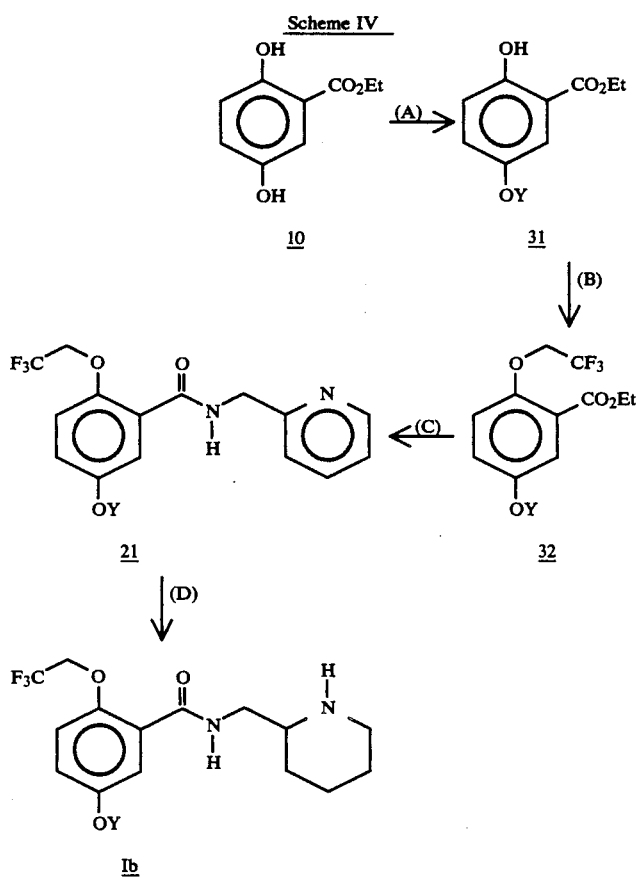

Step (A) of Scheme IV involves selective alkylation of the 5-hydroxyl group of ethyl 2,5-dihydroxybenzoate 10 with an appropriate electrophile as described in the above discussion of Scheme I to provide a compound of formula 31. In step (B), the compound of formula 31 is reacted with 2,2,2-trifluoroethyl trifluoromethane-sulfonate to provide a compound of formula 32. The ester moiety of the compound of formula 32 in step (C) is (1) hydrolyzed to the corresponding carboxylic acid, (2) activated toward nucleophilic attack by conventional means (e.g., converted to an acyl halide or treated with a carboxy activator such as dicyclohexylcarbodiimide (DCC)), and (3) reacted with 2-aminomethylpyridine to provide a compound of formula 21. The final step of the synthesis (step D) is hydrogenation of the pyridine ring to afford a compound of Formula Ib.

Compounds of Formula Ia or Ib wherein Y is a straight chain or branched chain alkyl carboxylic acid of 2 to 6 carbon atoms are prepared by hydrolysis of a corresponding ester formed via Schemes I, II, III or IV.

Compounds of Formula I wherein the group Y is susceptible of hydrogenolysis or hydrogenation must be prepared such that the group Y is not exposed to conditions under which it will be hydrogenolyzed or hydrogenated. Accordingly, Scheme V below is drawn particularly to the preparation of compounds of Formula Ic, wherein OY of Formula I is ortho to the benzamide carbonyl substituent, and wherein Y is straight chain or branched chain alkenyl or phenylalkenyl wherein the alkenyl group contains three to about six carbon atoms and wherein the unsaturation does not render the phenolic oxygen vinylic, or a secondary phenyl(lower)alkyl amide derivative of an alkyl carboxylic acid of 2 to about 6 carbon atoms wherein the amide nitrogen is benzylic.

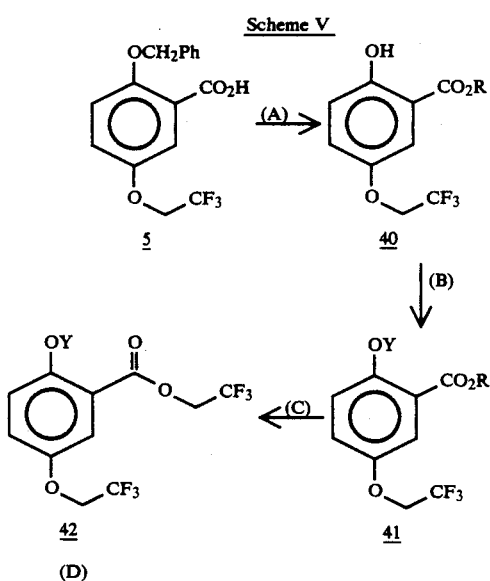

-continued
Scheme V

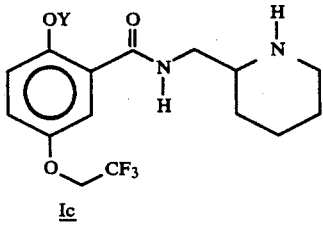

Compound 5 in Scheme V is prepared as described in the discussion of Scheme I above. Step (A) of Scheme V involves esterification of compound 5 by conventional methods and hydrogenalysis of the benylic protecting group as described above to afford a compound of formula 40 wherein R is lower alkyl, preferably ethyl. Step (B) is alkylation of phenolic oxygen, as described in the above discussion of Scheme I, to afford a compound of formula 41. In step (C) the compound of formula 41 is first hydrolysed to afford the corresponding carboxylic acid, and then re-esterified to afford a 2,2,2-trifluoroethyl ester of formula 42. Preferably the esterification step is carried out by treating the acid with 2,2,2-trifluoroethyl trifluoromethanesulfonate in the presence of a base such as potassium carbonate. Compounds of Formula Ic are then prepared in step (D) by nucleophilic displacement of the 2,2,2-trifluoroethoxide with the primary amino group of 2-aminomethylpiperidine.

Similarly, compounds of Formula I wherein OY is meta to the benzamide carbonyl substituent are prepared by the method of Scheme V, substituting compound 45 for compound 5 as starting material.

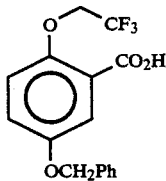

45

Compound 45 and a method of preparation therefor are disclosed in U.S. Pat. No. 4,339,587, which is incorporated herein by reference.

The activity of the compounds of the invention varies from compound to compound. The activity of compounds of the invention (or pharmaceutically acceptable acid-addition salts thereof) may be determined as described below by the ability of the compounds to block ouabain-induced ectopic ventricular tachycardia in pentobarbitalized male and female dogs weighing 8 to 14 kg.

The arrhythmia is produced according to the method outlined in Lucchesi, B. R., and Hardman, H. F.; The Influence of Dichloroisoproterenol (DCI) and Related Compounds Upon Ouabain and Acetylstrophanthidin Induced Cardiac Arrhythmias, J. Pharmacol. Exp. Therap., 1961, 132, 372, which is incorporated herein by reference. A toxic dose of ouabain is administered to an anesthetized dog in such a way that an ectopic ventricular tachycardia slowly develops (ectopic because stimulation of the distal end of the severed right vagus nerve does not alter the ventricular rate). The lack of a vagal response indicates that the pacemaker is no longer the SA node, but has shifted to a new location somewhere in the ventricle. An initial dose of ouabain, 40 μg/kg, is given intravenously and supplemented in 30 minutes with 20 μg/kg, and every 15 minutes thereafter with 10 μg/kg until ectopic ventricular tachycardia occurs. After the arrhythmia is allowed to stabilize for approximately 15 minutes, the test drug is administered by slow intravenous injection or by intraduodenal injection in 1.0 mg/kg increments approximately every five minutes until either the endpoint of sinus rhythm is attained or until a large dose has been given. When sinus rhythm is attained, peripheral vagal stimulation produces its characteristic response indicating a shift of the pacemaker back to the SA node. The duration of the sinus rhythm is recorded and a higher dose is then administered in an attempt to prolong the period of conversion.

By the test described above, preferred compounds of Formula I wherein the substituent OY is meta to the benzamide carbonyl substituent are those compounds wherein Y is straight chain alkyl of 1 to about 6 carbon atoms, straight chain alkylene carboxylic acid of 2 to about 6 carbon atoms or a derivative thereof selected from the group consisting of primary amides, secondary lower alkyl amides, secondary phenyl(lower)alkyl amides, tertiary amides wherein the amide substituents form a five- or six-membered saturated ring, tertiary amides wherein the amide substituents are independently lower alkyl, tertiary amides wherein one amide substituent is lower alkyl and the other is phenyl(lower)alkyl, and lower alkyl esters. Preferred compounds of Formula I wherein the substituent OY is ortho to the benzamide carbonyl substituent are those compounds wherein Y is a straight chain alkylene carboxylic acid of 2 to about 6 carbons, or a derivative thereof selected from the group consisting of primary amides, secondary lower alkyl amides, secondary phenyl(lower)alkyl amides, tertiary amides wherein the substituents form a five- or six-membered saturated ring, tertiary amides wherein the amide substituents are independently lower alkyl, tertiary amides wherein one amide substituent is lower alkyl and the other is phenyl(lower)alkyl, and lower alkyl esters; or a derivative of a straight chain hydroxyalkyl of 2 to about 6 carbon atoms selected from the group consisting of a phenyl ether or a lower alkyl ether; or ω-phenylalkyl wherein the alkyl group contains one to about three carbon atoms.

The most preferred compounds of the invention are:
(A) 5-(4-Ethoxycarbonylbutoxy)-N-(2-piperidylmethyl)-2-(2,2,2-trifluoroethoxy)benzamide hydrochloride hydrate;
(B) 2-(N-Isopropylcarbamoylmethoxy)-N-(2-piperidylmethyl)-5-(2,2,2-trifluoroethoxy)benzamide hydrochloride;
(C) 5-(N-Isopropylcarbamoylmethoxy)-N-(2-piperidylmethyl)-2-(2,2,2-trifluoroethoxy)benzamide acetate;
(D) 2-(2-Methoxyethoxy)-N-(2-piperidylmethyl)-5-(2,2,2-trifluoroethoxy)benzamide acetate;
(E) 2-[2-(1-Piperidyloxo)ethoxy]-N-(2-piperidylmethyl)-5-(2,2,2-trifluoroethoxy)benzamide hydrochloride hemihydrate;
(F) 2-(2-hydroxyethoxy)-N-(2-piperidylmethyl)-5-(2,2,2-trifluoroethoxy)benzamide acetate;
(G) 2-(3-Phenylpropoxy)-N-(2-piperidylmethyl)-5-(2,2,2-trifluoroethoxy)benzamide hydrochloride; and
(H) 2-(2-Ethoxyethoxy)-N-(2-piperidylmethyl)-5-(2,2,2-trifluoroethoxy)benzamide hydrochloride.

As a further test of antiarrhythmic activity, compounds (B), (D), (E), (F), and (G) above were tested for their ability to block aconitine-induced atrial arrhythmia. In this test, male and female dogs weighing 8 to 12 kilograms are anesthetized with a combination of pentobarbital sodium (30 mg/kg IV) and urethane (100 mg/kg IV). Blood pressure is recorded in the usual fashion, and a lead II electrocardiogram is recorded to visually monitor the arrhythmia.

Atrial flutter or fibrillation is produced according to a procedure described in Scherf, D., Studies on Auricular Tachycardia Caused by Aconitine Administration, Proc. Soc. Exp. Biol. Med., 1947, 64, 233, which is incorporated herein by reference. Under positive pressure artificial respiration with room air, the right side of the chest is opened at the fourth interspace and a pericardial cradle is prepared. A small cotton pledget is sutured to the atrium and saturated with 0.05% aqueous aconitine nitrate. The arrhythmia usually develops within a few minutes and is allowed to stabilize for approximately 15 minutes. The test compound is generally infused at the rate of either 0.1 or 0.2 mg/kg/min at a constant volume rate of 0.18 ml/min. The values for drug infusion rate and volume rate may be changed depending upon the relative potency and toxicity of the individual test compound. The infusion is continued either to the endpoint of sinus rhythm or until a large dose of the test compound has been given. The period of sinus rhythm is generally transient; however, the dose is usually increased in an effort to prolong the conversion period.

The several compounds tested by this method showed antiarrhythmic activity.

The compounds of the invention are generally active as antiarrhythmic agents. All compounds of the invention may be employed as the free base (or the zwitterion in cases wherein Y comprises a carboxylic acid moiety) or optionally as a pharmaceutically acceptable acid-addition salt thereof. Preferred salts include acetic, hydrochloric, sulfuric and phosphoric acid salts. Also useful are hydrobromic, sulfamic, methanesulfonic, benzenesulfonic, ethanedisulfonic, citric, maleic, oxalic, succinic, malic, fumaric, and tartaric acid salts. Pharmaceutically acceptable quaternary ammonium salts are useful as well.

In clinical practice, the antiarrhythmic compounds of the invention will be administered orally or by injection in the form of pharmaceutical compositions comprising a compound of the invention in the form of the free base or one of the common therapeutically acceptable salts, preferably the acetate or hydrochloride, in association with a pharmaceutically acceptable carrier. The carrier may be a solid, semi-solid or liquid diluent or an ingestible capsule. The active compound will be present in an amount effective to inhibit and/or prevent arrhythmia in a mammal. The amount of compound present will vary with the activities of the compound and the particular composition employed. Generally, the active compound will comprise between 0.01 percent and 5 percent of compositions intended for injection and between 10 percent and 80 percent of compositions intended for oral administration. Particularly preferred for intravenous administration are 0.05–1.0 percent aqueous solutions of the active compounds buffered with sodium acetate to pH of about 5–7. For oral administration, 20–60 percent formulations of the active ingredient in mannitol, lactose or potato starch are preferred.

Pharmaceutical compositions in the form of dosage units for oral administration, which compositions contain the compound of the invention in the form of the free base or a pharmaceutically acceptable acid addition salt, may be prepared in various ways. The compounds may be mixed with a solid pulverulent carrier, for example lactose, saccharose, sorbitol, mannitol, a starch such as potato starch, corn starch or amylopectin, a cellulose derivative, or gelatin. The carrier may also be a lubricant such as magnesium or calcium stearate, a Carbowax R or other polyethylene glycol wax. A composition may be compressed to form tablets, or, preferably, cores which are then coated with a concentrated sugar solution which may contain, for example, gum arabic, gelatin, talcum and/or titanium dioxide.

Ingestible capsules which may be used include hard or soft gelatin capsules. Soft gelatin capsules (pearl-shaped closed capsules) and other closed capsules consist, for example, of a mixture of gelatin and glycerol, and contain, for example, mixtures of the active substance with a vegetable oil. Hard gelatin capsules contain, for example, granulates of the active substance with solid, pulverulent carriers such as lactose, saccharose, sorbitol, mannitol; starches such as potato starch, corn starch, or amylopectin; cellulose derivatives or gelatin, as well as magnesium stearate or stearic acid.

For parenteral application by injection, the composition comprises an aqueous, generally saline, solution of a water-soluble, pharmaceutically-acceptable salt of the active compound and optionally also a stabilizing agent and/or a buffer such as sodium acetate.

The following examples are provided to illustrate the invention. They are not intended to limit the invention.

EXAMPLE I

Preparation of 2-(4-Carboxybutoxy)-N-(2-piperidylmethyl)-5-(2,2,2-trifluoroethoxy)benzamide

Part A

Under a nitrogen atmosphere, 3.5 g of 60% sodium hydride in mineral oil is washed twice with hexane and then suspended in 80 ml of dry dimethylformamide. A solution of 22.5 g (0.069 mole) of 2-hydroxy-N-(2-pyridylmethyl)-5-(2,2,2-trifluoroethoxy)benzamide in 100 ml of dimethylformamide is added dropwise to the sodium hydride suspension to give a thick foam. After the addition is complete the reaction mixture is stirred for 30 minutes at about 25° C. and for another 30 minutes at about 60° C. A solution of 20.2 g (0.097 mole) of 5-bromovaleric acid ethyl ester in 40 ml of dimethylformamide is added dropwise with stirring to the reaction mixture. The resulting pale brown solution is allowed to stir at about 60° C. for about 16 hours. The solution is poured into about 1 liter of cold water and then chilled. The resulting precipitate is collected, rinsed with cold water and then dissolved in chloroform. The chloroform solution is washed through a short Florisil ® column and the eluent is evaporated to give 28.3 g of an ivory, waxy solid. This material is recrystallized from about 280 ml of 2:1 ethanol:water to give 23.1 g of ivory crystalline 2-(4-ethoxycarbonyl-butoxy(-N-(2-pyridylmethyl)-5-(2,2,2-trifluoroethoxy)-benzamide, m.p. 88°–90° C.

Part B

Under a nitrogen atmosphere a solution of 23.0 g of the material from Part A in 300 ml of acetic acid was added to a paste of 1.5 g platinum oxide/acetic acid in a 500 ml Parr bottle. The mixture was hydrogenated on a Parr apparatus for about 18 hours and then filtered to remove catalyst. The filtrate was concentrated to give 32 g of a clear, viscous syrup. The syrup was dissolved in about 500 ml of water and the resulting solution was basified with 10% sodium carbonate to give a white solid. The solid was collected, rinsed twice with water and then dissolved in chloroform. The chloroform solution was washed with brine, dried with magnesium sulfate and then evaporated to give 17.5 g of an ivory solid. This solid was recrystallized from about 300 ml of 4:1 heptane:toluene to give 14.7 g of white 2-(4-ethoxycarbonylbutoxy)-N-(2-piperidylmethyl)- 5-(2,2,2-trifluoroethoxy)benzamide, m.p. 100°–101.5° C.

Part C

A solution of 1.22 g (0.030 mole) of sodium hydroxide in 75 ml of water was added to a suspension of 11.2 g of material from Part B in 75 ml of ethanol. The reaction mixture was allowed to stir at about 25° C. for about 16 hours. The resulting solution was concentrated (bath temperature kept below 50° C.) to remove the ethanol. The concentrate was diluted with about 200 ml of water and then filtered using added Super Cel ®. The resulting solution was treated with 10% hydrochloric acid to adjust the pH to 7–8 and then chilled. The precipitate was collected, rinsed with cold water and then vacuum dried to give 9.3 g of a white solid. This solid was recrystallized from about 170 ml of methanol to give 7.5 g of feathery white solid 2-(4-carboxybutoxy)-N-(2-piperidylmethyl)-5-(2,2,2-trifluoroethoxy)benzamide, m.p. 196°–198° C. Analysis: Calculated for: $C_{20}H_{27}F_3N_2O_5$: %C, 55.55; %H, 6.3; %N, 6.5; Found: %C, 55.7; %H, 6.4; %N, 6.4.

EXAMPLE II

Preparation of 2-(4-Ethoxycarbonylbutoxy)-N-(2-piperidylmethyl)-5-(2,2,2-trifluoroethoxy)benzamide Acetate A solution of 3.25 g of 2-(4-ethoxycarbonyl-butoxy)-N-(2-piperidylmethyl)-5-(2,2,2-trifluoroethoxy)benzamide, prepared according to Part B of Example I, in about 10 ml of acetic acid was warmed briefly on a steam bath, cooled and then concentrated to give 4.4 g of a greasy damp solid. This material was triturated with diethyl ether to give an ivory powder. The powder was recrystallized from 35 ml of ethyl acetate using Darco ® and Super Cel ® to give 2.3 g of white powdery 2-(4-ethoxycarbonylbutoxy)-N-(2-piperidylmethyl)-5-(2,2,2trifluoroethoxy)benzamide acetate, m.p. 114°–116° C.

Analysis: Calculated for $C_{24}H_{35}F_3N_2O_7$: %C, 55.4; %H, 6.8; N, 5.4; Found: %C, 55.5; %H, 6.9; %N, 5.2.

EXAMPLE III

Preparation of 2-(Ethoxycarbonylmethoxy)-N-(2-piperidylmethyl)-5-(2,2,2-trifluoroethoxy)benzamide Hydrochloride

Part A

Using the general method of Example I Part A, 9.8 g (0.03 mole) of 2-hydroxy-N-(2-pyridylmethyl)-5-(2,2,2-trifluoroethoxy)benzamide was reacted with 7.0 g (0.042 mole) of ethyl bromoacetate to give 7.6 g of ivory powdery -(ethoxycarbonylmethoxy)-N-(2-pyridylmethyl)-5-(2,2,2-trifluoroethoxy)benzamide, m.p. 109°–111° C.

Part B

Using the general method of Example I Part B, the material from Part A was hydrogenated to give 6.6 g of white powdery 2-(ethoxycarbonylmethoxy)-N-(2-piperidylmethyl)-5-(2,2,2-trifluoroethoxy)benzamide.

Part C

Ethanol saturated with hydrochloric acid was added dropwise to a solution of 3.2 g of the free base from Part B in a small amount of warm ethanol until the solution changed from basic to acidic. A thick precipitate formed within minutes. Enough ethanol was added to bring the total volume to about 90 ml and the mixture was warmed to dissolution, filtered with Darco ®, refiltered with Super Cel ® and then allowed to cool. The precipitate was collected, rinsed twice with cold ethanol, twice with diethyl ether and then vacuum dried to give 2.4 g of white powdery 2-(ethoxycarbonylmethoxy)-N-(2-piperidylmethyl)-5-(2,2,2-trifluoroethoxy)benzamide hydrochloride, m.p. 216°–217° C. (decomposition). Analysis: Calculated for $C_{19}H_{25}F_3N_2O_5 \cdot HCl$: %C, 50.2; %H, 5.8; %N, 6.2; Found: %C, 50.2; %H, 5.8; %N, 6.2.

EXAMPLE IV

Preparation of 2-(4-Carbamoylbutoxy)-N-(2-piperidylmethyl)-5-(2,2,2-trifluoroethoxy)benzamide Acetate

Part A

Using the general method of Example I Part A, 4.7 g (0.014 mole) of 2-hydroxy-N-(2-pyridylmethyl)-5-(2,2,2-trifluoroethoxy)benzamide was reacted with 2.3 g (0.013 mole) of 5-bromovaleramide to give 3.7 g of white powdery 2-(4-carbamoylbutoxy)-N-(2-pyridylmethyl)-5-(2,2,2-trifluoroethoxy)benzamide, m.p. 178°–180° C. Analysis: Calculated for $C_{20}H_{22}F_3N_3O_4$: %C, 56.5; %H, 5.2; %N, 9.9; Found: %C, 56.7; %H, 5.2; %N, 9.9.

Part B

A solution of 3.5 g of material from Part A in 75 ml of acetic acid was added to a paste of 0.3 g of platinum oxide/acetic acid and hydrogenated on a Parr apparatus. The reaction mixture was filtered to remove the catalyst and then concentrated to a viscous syrup. The syrup was triturated with ether to give a white solid which was recrystallized from acetonitrile to give 2.9 g of white 2-(4-carbamoylbutoxy)-N-(2-piperidylmethyl)-5-(2,2,2-trifluoroethoxy)benzamide acetate m.p. 138°–141° C. Analysis: Calculated for $C_{20}H_{28}F_3N_3O_4 \cdot C_2H_4O_2$: %C, 53.8; %H, 6.6; %N, 8.5; Found: %C, 53.7; %H, 6.5; %N, 8.5.

EXAMPLE V

Preparation of 5-(4-Carboxybutoxy)-N-(2-piperidylmethyl)-2-(2,2,2-trifluoroethoxy)benzamide Hydrochloride

Part A

Using the method of Example I Part A, 13.1 g (0.04 mole) of 5-hydroxy-N-(2-pyridylmethyl)-2-(2,2,2-trifluoroethoxy)benzamide was reacted with 11.7 g (0.056 mole) of ethyl 5-bromovalerate to give 13.7 g of white 5-(4-ethoxycarbonylbutoxy))-N-(2-pyridylmethyl)-2-(2,2,2-trifluoroethoxy)benzamide, m.p. 83°–84° C.

Part B

Using the method of Example IV Part B, 13.6 g of the material from Part A was hydrogenated to give 10.2 g of white powdery 5-(4-ethoxycarbonylbutoxy)-N-(2-piperidylmethyl)-2-(2,2,2-trifluoroethoxy)benzamide acetate.

Part C

A suspension of 5.9 g of the acetate salt from Part B in 125 ml of water was made basic with 10% sodium carbonate and the resulting solid was taken up in chloroform. The chloroform extract was dried with magnesium sulfate and then evaporated to give 5.2 g of an ivory solid. To a suspension of this solid in 35 ml of ethanol was added 0.57 g of sodium hydroxide in 35 ml of water. The resulting mixture was allowed to stir at about 25° C. for about 16 hours before being concentrated to remove most of the ethanol. The resulting hazy solution was diluted with about 50 ml of water and then filtered through Super Cel ®. The pH of the filtrate was adjusted to pH 7–8 with 10% hydrochloric acid and the resulting precipitate was collected and dried in a vacuum oven to give 4.0 g of a white powder. This powder was suspended in 120 ml of hot water; enough dilute hydrochloric acid was added to make the suspension acidic and then heating was continued until all the material dissolved. The hot solution was filtered through a layer of Super Cel ® and cooled to give 3.6 g of white powdery 5-(4-carboxybutoxy)-N-(2-piperidylmethyl)-2-(2,2,2-trifluoroethoxy)benzamide hydrochloride, m.p. 212°–214° C. Analysis Calculated for $C_{20}H_{27}F_3N_2O_5 \cdot HCl$: %C, 51.2; %H, 6.0; %N, 6.0; Found: %C, 51.1; %H, 6.1; %N, 6.0.

EXAMPLE VI

Preparation of 5-(4-Ethoxycarbonylbutoxy)-N-(2-piperidylmethyl)-2-(2,2,2-trifluoroethoxy)benzamide Hydrochloride Hydrate 4.0 g of the acetate salt from Example V Part B was recrystallized from 40 ml of ethyl acetate to give 3.3 g of white powder, m.p. 91°–93° C. This material was dissolved in water and the solution was made basic with 10% sodium carbonate to give a white precipitate which was taken up in methylene chloride. The methylene chloride extract was washed with brine, dried with magnesium sulfate and then evaporated to give 2.7 g of the free base. This material was dissolved in ethanol, acidified with an ethanolic solution of hydrochloric acid, filtered warm and then cooled to give a white precipitate. The precipitate was collected and dried to give 2.4 g of white crystalline 5-(4-ethoxycarbonylbutoxy)-N-(2-piperidylmethyl)-2-(2,2,2-trifluoroethoxy)benzamide hydrochloride hydrate, m.p. 145°–148° C. Analysis: Calculated for $C_{22}H_{31}F_3N_2O_5 \cdot HCL \cdot H_2O$: %C, 51.3; %H, 6.6; %N, 5.4; Found: %C, 51.8; %H, 6.4; %N, 5.5.

EXAMPLE VII

Preparation of 2-(N-Isopropylcarbamoylmethoxy)-N-(2-piperidylmethyl)-5-(2,2,2-trifluoroethoxy)benzamide Hydrochloride

Part A

Using the general method of Example I Part A, 3.9 g (0.012 mole) of 2-hydroxy-N-(2-pyridylmethyl)-5-(2,2,2-trifluoroethoxy)benzamide was reacted with 2.0 g (0.011 mole) of N-isopropyl bromoacetamide to give 3.8 g of white solid 2-(N-isopropylcarbamoylmethoxy)-N-(2-pyridylmethyl)-5-(2,2,2-trifluoroethoxy)benzamide, m.p. 124°–126° C.

Part B

A solution of 3.2 g of the material from Part A in 60 ml of acetic acid was added to a paste of 0.25 g platinum oxide/acetic acid and hydrogenated on a Parr apparatus. The reaction mixture was filtered and then concentrated to give a syrup. The syrup was dissolved in water, made basic with 10% sodium carbonate then extracted with methylene chloride. The methylene chloride extract was washed with brine then evaporated to give 2.9 g of a sticky ivory solid. This material was dissolved in a minimum amount of ethanol, acidified with ethanol saturated with hydrochloric acid, allowed to stand for a few minutes and then slowly added to about 200 ml of diethyl ether. The resulting suspension was chilled and then filtered to give 2.2 g of a white powder. The powder was recrystallized from about 225 ml of acetonitrile to give 1.8 g of fluffy white solid 2-(N-isopropylcarbamoylmethoxy)-N-(2-piperidylmethyl)-5-(2,2,2-trifluoroethoxy)benzamide hydrochloride, m.p. 216°–218° C. Analysis: Calculated for $C_{20}H_{28}F_3N_3O_4 \cdot HCl$: %C, 51.3; %H, 6.25; %N, 9.0; Found: %C, 51.4; %H, 6.3; %N, 8.8.

EXAMPLE VIII

Preparation of 5-(4-Carbamoylbutoxy)-N-(2-piperidylmethyl)-2-(2,2,2-trifluoroethoxy)benzamide Acetate

Part A

Using the general method of Example I Part A, 6.5 g (0.02 mole) of 5-hydroxy-N-(2-pyridylmethyl)-2-(2,2,2-trifluoroethoxy)benzamide was reacted with 3.3 g (0.018 mole) of 5-bromovaleramide to give 3.5 g of white powdery 5-(4-carbamoylbutoxy)-N-(2-pyridylmethyl)-2-(2,2,2-trifluoroethoxy)benzamide, m.p.138°–139° C.

Part B

Using the general method of Example IV Part B, the material from Part A was hydrogenated to give 2.5 g of white powdery 5-(4-carbamoylbutoxy)-N-(2-piperidylmethyl)-2-(2,2,2-trifluoroethoxy)benzamide acetate, m.p. 154°–156° C. Analysis: Calculated for $C_{20}H_{28}F_3N_3O_4 \cdot C_2H_4O_2$: %C, 53.8; %H, 6.6; %N, 8.5; Found: %C, 54.0; %H, 6.7; %N, 8.4.

EXAMPLE IX

Preparation of 5-(N-Isopropylcarbamoylmethoxy)-N-(2-piperidylmethyl)-2-(2,2,2-trifluoroethoxy)benzamide Acetate

Part A

Using the general method of Example I Part A, 6.5 g (0.02 mole) of 5-hydroxy-N-(2-pyridylmethyl)-2-(2,2,2-trifluoroethoxy)benzamide was reacted with 3.3 g (0.018 mole) of N-isopropyl bromoacetamide to give 2.7 g of tiny white flakes of 5-(N-isopropylcarbamoylmethoxy)-N-(2-pyridylmethyl)-2-(2,2,2-trifluoroethoxy)benzamide, m.p. 124°–126° C.

Part B

Using the general method of Example IV Part B, 2.6 g of material from Part A was hydrogenated to give 1.5 g of white solid 5-(N-isopropylcarbamoylmethoxy)-N-(2-piperidylmethyl)-2-(2,2,2-trifluoroethoxy)benzamide acetate, m.p. 132°–135° C. Analysis: Calculated for $C_{20}H_{28}F_3N_3O_4 \cdot C_2H_4O_2$: %C, 53.8; %H, 6.6; %N, 8.55; Found: % C, 54.4; %H, 6.8; %N, 8.8.

EXAMPLE X

Preparation of 5-(Ethoxycarbonylmethoxy)-N-(2-piperidylmethyl)-2-(2,2,2-trifluoroethoxy)benzamide Hydrochloride

Part A

Using the general method of Example I Part A, 10.4 g (0.032 mole) of 5-hydroxy-N-(2-pyridylmethyl)-2-(2,2,2-trifluoroethoxy)benzamide was reacted with 7.45 g (0.045 mole) of ethyl bromoacetate to give 5.0 g of ivory powdery 5-(ethoxycarbonylmethoxy)-N-(2-pyridylmethyl)-2-(2,2,2-trifluoroethoxy)benzamide, m.p. 73°–76° C.

Part B

Using the general method of Example III Parts B and C, 4.9 g of the material from Part A was converted to 2.8 g of white powdery 5-(ethoxycarbonylmethoxy)-N-(2-piperidylmethyl)-2-(2,2,2-trifluoroethoxy)benzamide hydrochloride, m.p. 175°–177° C. Analysis: Calculated for $C_{19}H_{25}F_3N_2O_5 \cdot HCL$: %C, 50.2; %H, 5.8; %N, 6.2; Found: %C, 49.9; %H, 5.7; %N, 6.0.

EXAMPLE XI

Preparation of 2-(2-Methoxyethoxy)-N-(2-piperidylmethyl)-5-(2,2,2-trifluoroethoxy)benzamide Acetate

Part A

Using the general method of Example I Part A, 6.5 g (0.02 mole) of 2-hydroxy-N-(2-pyridylmethyl)-5-(2,2,2-trifluoroethoxy)benzamide was reacted with 3.9 g (0.028 mole) of 2-bromoethyl methyl ether to give 5.2 g of white crystalline 2-(2-methoxyethoxy)-N-(2-pyridylmethyl)-5-(2,2,2-trifluoroethoxy)benzamide, m.p. 104°–107° C.

Part B

Using the general method of Example IV Part B, 5.0 g of the material from Part A was hydrogenated to give 4.4 g of white crystalline 2-(2-methoxyethoxy)-N-(2-piperidylmethyl)-5-(2,2,2-trifluoroethoxy)benzamide acetate, m.p. 125°–128° C. Analysis: Calculated for $C_{18}H_{25}F_3N_2O_4 \cdot C_2H_4O_2$: %C, 53.3; %H, 6.5; %N, 6.2; Found: %C, 53.4; %H, 6.5; %N, 6.1.

EXAMPLE XII

Preparation of 2-Carbamoylmethoxy-N-(2-piperidylmethyl)-5-(2,2,2-trifluoroethoxy)benzamide Hydrochloride Hemihydrate

Part A

A solution of 6.5 g (0.02 mole) of 2-hydroxy-N-(2-pyridylmethyl)-5-(2,2,2-trifluoroethoxy)benzamide in 20 ml of dimethylformamide was added dropwise to a suspension of 0.021 mole of sodium hydride in 10 ml dimethylformamide. The resulting mixture was stirred at about 25° C. for 30 minutes, at 60° C. for 30 minutes, and then 0.3 g of sodium iodide was added followed by the addition of a solution of 1.7 g (0.018 mole) of 2-chloroacetamide in 15 ml dry dimethylformamide. The reaction mixture was stirred for about 16 hours at 60° C. and then poured into 500 ml cold water. The resulting precipitate was collected and dried, then dissolved in a minimum of 5% methanol in chloroform and washed through a column of basic alumina. The eluent was evaporated to give a white solid which was recrystalized from about 300 ml of 3:4 water:ethanol to give 4.9 g of white crystalline 2-carbamoylmethoxy-N-(2-pyridylmethyl)-5-(2,2,2-trifluoroethoxy)benzamide.

Part B

Using the general method of Example III Parts B and C, the material from Part A provided 3.3 g of white solid 2-carbamoylmethoxy-N-(2-piperidylmethyl)-5-(2,2,2-trifluoroethoxy)benzamide hydrochloride hemihydrate, m.p. 203°–206° C. Calculated for $C_{17}H_{22}F_3N_3O_4 \cdot HCL \cdot \frac{1}{2}H_2O$: %C, 46.95; %H, 5.6; %N, 9.7; Found: %C, 46.6; %H, 5.3; %N, 9.5.

EXAMPLE XIII

Preparation of 2-[2-(1-Piperidyloxo)ethoxy]-N-(2-piperidylmethyl)-5-(2,2,2-trifluoroethoxy)benzamide Hydrochloride Hemihydrate

Part A

Using the general method of Example XII Part A, 6.5 g (0.02 mole) of 2-hydroxy-N-(2-pyridylmethyl)-5-(2,2,2-trifluoroethoxy)benzamide was reacted with 3.7 g (0.018 mole) of 1-bromoacetylpiperidine to provide 5.5 g of off white crystalline 2-[2-(1-piperidyloxo)ethoxy]-N-(2-pyridylmethyl)-5-(2,2,2-trifluoroethoxy)benzamide, m.p.139°–142° C.

Part B

Using the general method of Example III Parts B and C, the material from Part A provided 1.9 g of white crystalline 2-[2-(1-piperidyloxo)ethoxy]-N-(2-piperidylmethyl)-5-(2,2,2-trifluoroethoxy)benzamide hydrochloride hemihydrate, m.p.125°–132° C. Analysis: Calculated for $C_{22}H_{30}F_3N_3O_4 \cdot HCL \cdot \frac{1}{2}H_2O$: %C, 52.5; %H, 6.4; % N, 8.4; Found: %C, 52.7; %H, 6.7; %N, 8.2.

EXAMPLE XIV

Preparation of 2-Allyloxy-N-(2-piperidylmethyl)-5-(2,2,2-trifluoroethoxy)benzamide Hydrochloride A solution of 101.6 g of 2-benzyloxy-5-(2,2,2-trifluoroethoxy)benzoic acid (Part F of the synthesis of 2-hydroxy-N-(2-pyridylmethyl)-5-(2,2,2-trifluoroethoxy)benzamide in Example XXII below), 400 ml of absolute ethanol and about 8 ml of concentrated sulfuric acid was heated at reflux for about 16 hours. The resulting brown solution was concentrated to about one third its original volume then diluted with cold water and extracted twice with diethyl ether. The ether extracts were combined, washed twice with water, once with 5% sodium bicarbonate, once with brine and then evaporated to give 102 g of a mixture of ivory needles and an orange liquid. This material was recrystallized from about 500 ml of heptane to give 87.6 g of white crystalline ethyl 2-benzyloxy-5-(2,2,2-trifluoroethoxy)benzoate, m.p. 54°–57° C. The structure was confirmed by nuclear magnetic resonance spectroscopy.

Part B

Under a nitrogen atmosphere, a solution of 76.3 g of material from Part A in 1210 ml of ethanol was added to a paste of 2.0 g of 10% paladium on carbon and hydrogenated on a Parr apparatus. The reaction mixture was filtered then evaporated to provide a gray syrup which was put through a short Florosil ® column. The eluent was evaporated to give 57 g of white solid ethyl 2-hydroxy-5-(2,2,2-trifluoroethoxy)benzoate, m.p. 35°–38° C.

Part C

A solution of 7.65 g (0.029 mole) of material from Part B in 50 ml of dimethylformamide was added dropwise to a suspension of 0.0375 mole of sodium hydride in 40 ml of dimethylformamide and allowed to stir at about 25° C. for about 16 hours. The reaction mixture was heated to 60° C. and then a solution of 5.08 g (0.042 mole) of allyl bromide in 20 ml of dimethylformamide was added dropwise. After five hours of stirring at 60° C. an additional 0.1 g of sodium hydride was added. This addition caused the reaction to become cloudy; heating and stirring were continued until the reaction cleared and thin layer chromatography showed no remaining starting material. The reaction mixture was poured into about 300 ml of cold water then extracted 3 times with diethyl ether. The ether extracts were combined, washed with brine and then evaporated to give 8.8 g of ethyl 2-allyloxy-5-(2,2,2-trifluoroethoxy)benzoate as an orange syrup.

Part D

A solution of the material from Part C in about 100 ml of ethanol was combined with a solution of 1.5 g of sodium hydroxide in 100 ml of water and heated at reflux for about 16 hours. The reaction mixture was concentrated to remove the ethanol and then diluted with about 400 ml of cold water. The solution was acidified with 10% hydrochloric acid then cooled in an ice bath. The resulting precipitate was collected then put through a short column of Florosil ®. The eluent was evaporated to give 7.2 g of white solid 2-allyloxy-5-(2,2,2-trifluoroethoxy)benzoic acid, m.p. 59°–63° C. The structure was confirmed by nuclear magnetic resonance spectroscopy.

Part E

The material from Part D was combined with 4.0 g of potassium carbonate and 125 ml of acetone and then heated at reflux for about two hours. A solution of 9.1 g of 2,2,2-trifluoroethyl trifluoromethanesulfonate in 50 ml of acetone was added dropwise to the reaction mixture. The resulting mixture was heated at reflux for about 16 hours, cooled and then concentrated to remove most of the acetone. The residue was diluted with water and ether. The aqueous layer was extracted twice with ether. The combined ether extracts were washed with brine and then evaporated to give 9.0 g of 2,2,2-trifluoroethyl 2-allyloxy-5-(2,2,2-trifluoroethoxy)benzoate as a clear liquid.

Part F

A solution of the material from Part E in 20 ml of 1,2-dimethoxyethane was added dropwise to a solution of 5.7 g of 2-aminomethylpiperidine in 20 ml of 1,2-dimethoxyethane. The reaction mixture was stirred at about 25° C. for about 2 hours, refluxed gently for 1 hour then stirred at about 25° C. for about 16 hours. Thin layer chromatography of a sample showed starting material so 1.0 g of 2-aminomethylpiperidine was added and the reaction refluxed for about 1.5 hours. Thin layer chromatography of a sample showed no change. The reaction mixture was concentrated to about one third its original volume, diluted with about 200 ml of cold water and then chilled in an ice bath. The resulting yellow precipitate was collected, washed thoroughly with cold water and then put through a short column of basic alumina. The eluent was concentrated to give 8.7 g of a pale yellow solid which was recrystallized from about 300 ml of hexane to give 7.3 g of a white powder. This powder was dissolved in about 225 ml of diethyl ether and the pH of the solution was adjusted to about pH 1 using diethyl ether saturated with hydrochloric acid. The resulting precipitate was collected and recrystallized twice from 2:1 isopropanol:ethanol to provide 5.9 g of white crystalline 2-allyloxy-N-(2-piperidylmethyl)-5-(2,2,2-trifluoroethoxy)benzamide hydrochloride, m.p. 236°–238° C. Analysis: Calculated for $C_{18}H_{23}F_3N_2O_3 \cdot HCL$: %C, 52.9; %H, 5.9; %N, 6.9; Found: %C, 53.0; %H, 6.0; %N, 6.6.

EXAMPLE XV

Preparation of 2-(2-Hydroxyethoxy)-N-(2-piperidylmethyl)-5-(2,2,2-trifluoroethoxy)benzamide Acetate

Part A

Using the general method of Example I Part A, 6.5 g (0.02 mole) of 2-hydroxy-N-(2-pyridylmethyl)-5-(2,2,2-trifluoroethoxy)benzamide was reacted with 3.5 g (0.028 mole) of 2-bromoethanol to give 3.6 g of ivory solid 2-(2-hydroxyethoxy)-N-(2-pyridylmethyl)-5-(2,2,2-trifluoroethoxy)benzamide, m.p. 120°–123° C.

Part B

Using the general method of Example IV Part B, the material from Part A was hydrogenated to provide 1.9 g of white powdery 2-(2-hydroxyethoxy)-N-(2-piperidylmethyl)-5-(2,2,2-trifluoroethoxy)benzamide acetate, m.p. 149°–151° C. Analysis: Calculated for $C_{17}H_{23}F_3N_2O_4 \cdot C_2H_4O_2$: %C, 52.3; %H, 6.2; %N, 6.4; Found: %C, 52.4; %H, 6.2; %N, 6.4.

EXAMPLE XVI

Preparation of 2-(3-Phenyl-2-propenyloxy)-N-(2-piperidylmethyl)-5-(2,2,2-trifluoroethoxy)benzamide Hydrochloride Using the general method of Example XIV Parts C thru F, 8.3 g (0.042 mole) of cinnamyl bromide was reacted to give 0.9 g of white crystalline 2-(3-phenyl-2-propenyloxy)-N-(2-piperidylmethyl)-5-(2,2,2-trifluoroethoxy)benzamide hydrochloride, m.p. 190°–192° C. Analysis: Calculated for $C_{24}H_{27}F_3N_2O_3 \cdot HCL$: %C, 59.4; %H, 5.8; %N, 5.8; Found: %C, 59.5; %H, 5.7; %N, 5.7.

EXAMPLE XVII

Preparation of 2-(3-Phenylpropoxy)-N-(2-piperidylmethyl)-5-(2,2,2-trifluoroethoxy)benzamide Hydrochloride Using the general method of Example XIV Parts C through F, 8.36 g (0.042 mole) of 3-phenylpropyl bromide was reacted to provide 4.5 g of white powdery 2-(3-phenylpropoxy)-N-(2-piperidylmethyl)-5-(2,2,2-trifluoroethoxy)benzamide hydrochloride, m.p. 154°–157° C. Analysis: Calculated for $C_{24}H_{29}F_3N_2O_3 \cdot HCL$: %C, 59.2; %H, 6.2; %N, 5.7; Found: %C, 59.1; %H, 6.2; %N, 5.6.

EXAMPLE XVIII

Preparation of 2-(3-Phenoxypropoxy)-N-(2-piperidylmethyl)-5-(2,2,2-trifluoroethoxy)benzamide Hydrochloride Using the general method of Example XIV Parts C through F, 9.0 g (0.042 mole) of 3-phenoxypropyl bromide was reacted to provide 3.6 g of white powdery 2-(3-phenoxypropoxy)-N-(2-piperidylmethyl)-5-(2,2,2-trifluoroethoxy)benzamide hydrochloride, m.p. 168°–170° C. Analysis: Calculated for $C_{24}H_{29}F_3N_2O_4 \cdot HCL$: %C, 57.3; %H, 6.0; %N, 5.6; Found: %C, 57.6; %H, 6.0; %N, 5.5.

EXAMPLE XIX

Preparation of 2-(2-Ethoxyethoxy)-N-(2-piperidylmethyl)-5-(2,2,2-trifluoroethoxy)benzamide Hydrochloride

Part A

Using the general method of Example I Part A, 4.3 g (0.028 mole of 2-bromoethyl ethyl ether was reacted with 6.52 g (0.02 mole) of 2-hydroxy-N-(2-pyridylmethyl)-5-(2,2,2-trifluoroethoxy)benzamide to provide 2.8 g of white crystalline 2-(2-ethoxyethoxy)-N-(2-pyridylmethyl)-5-(2,2,2-trifluoroethoxy)benzamide, m.p. 90°–94° C. The structure was confirmed by nuclear magnetic resonance spectroscopy.

Part B

Using the general method of Example III Parts B and C, the material from Part A was reacted to provide 1.1 g of white crystalline 2-(2-ethoxyethoxy)-N-(2-piperidylmethyl)-5-(2,2,2-trifluoroethoxy)benzamide hydrochloride, m.p. 204°–207° C. Analysis: Calculated for $C_{19}H_{27}F_3N_2O_4 \cdot HCL$: %C, 51.8; %H, 6.4; %N, 6.4; %C, 52.0; %H, 6.4; %N, 6.4.

EXAMPLE XX

Preparation of 5-(2-Methoxyethoxy)-N-(2-piperidylmethyl)-2-(2,2,2-trifluoroethoxy)benzamide Acetate

Part A

Using the general method of Example I Part A, 3.9 g (0.028 mole) of 2-bromoethyl methyl ether was reacted with 6.52 g (0.02 mole) of 5-hydroxy-N-(2-pyridylmethyl)-2-(2,2,2-trifluoroethoxy)benzamide to provide 5.1 g of white solid 5-(2-methoxyethoxy)-N-(2-pyridylmethyl)-2-(2,2,2-trifluoroethoxy)benzamide. The structure was confirmed by nuclear magnetic spectroscopy.

Part B

Using the general method of Example IV Part B, the material from Part A was hydrogenated to provide 4.8 g of white powdery 5-(2-methoxyethoxy)-N-(2-piperidylmethyl)-2-(2,2,2-trifluoroethoxy)benzamide acetate, m.p. 130°–132° C. Analysis: Calculated for $C_{18}H_{25}F_3N_2O_4 \cdot C_2H_4O_2$: %C, 53.3; %H, 6.5; %N, 6.2; Found: %C, 53.3; %H, 6.5; %N, 6.1.

EXAMPLE XXI

Preparation of 2-(N-Phenethylcarbamoylmethoxy)-N-(2-piperidylmethyl)-5-(2,2,2-trifluoroethoxy)benzamide Hydrochloride

Part A

Using the general method of Example I Part A, 5.1 g (0.02 mole) of N-phenethyl bromoacetamide was reacted with 4.9 g (0.015 mole) of 2-hydroxy-N-(2-pyridylmethyl)-5-(2,2,2-trifluoroethoxy)benzamide to provide 2.6 g of crystalline 2-(N-phenethylcarbamoylmethoxy)-N-(2-pyridylmethyl)-5-(2,2,2-trifluoroethoxy)benzamide, m.p. 140°–142° C. The structure was confirmed by nuclear magnetic resonance spectroscopy.

Part B

Using the general method of Example III Parts B and C, the material from Part A was hydrogenated to provide 1.1 g of white crystalline 2-(N-phenethylcarbamoylmethoxy)-N-(2-piperidylmethyl)-5-(2,2,2-trifluoroethoxy)benzamide hydrochloride, m.p. 169°–171° C. Analysis: Calculated for $C_{25}H_{30}F_3N_3O_4 \cdot HCL$: %C, 56.7; %H, 5.9; %N, 7.9; Found: %C, 56.2; %H, 6.6; %N, 7.7.

EXAMPLE XXII

Preparation of 2-Hydroxy-N-(2-pyridylmethyl)-5-(2,2,2-trifluoroethoxy)benzamide

Part A

A solution of 49.3 g (0.36 mole) potassium carbonate and 3 g of sodium iodide in 300 ml of water was combined with 60.3 g (0.3 mole) of 5-bromosalicylaldehyde, 45.6 g (0.36 mole) of benzyl chloride and 240 ml of 1,2-dimethoxyethane and refluxed for about 16 hours. The reaction mixture was cooled, concentrated to remove most of the 1,2-dimethoxyethane, diluted with cold water and then extracted twice with methylene chloride. The extracts were combined, washed with brine, dried and evaporated to provide 91 g of a brown solid. The solid was recrystallized from 550 ml of 4:1 heptane:toluene to provide 75.7 g of yellow crystalline 5-bromo-2-benzyloxybenzaldehyde, m.p. 70°–73° C. The infrared and nuclear magnetic resonance spectra of this product were consistent with the assigned structure.

Part B

To a solution of 120.5 (0.4139 mole) of 5-bromo-2-benzyloxybenzaldehyde and 30.8 g (0.04967 mole) of ethylene glycol in 600 ml of benzene was added 1.0 g of p-toluenesulfonic acid. The reaction was heated at reflux and a Dean-Stark trap was used to separate the water. After four hours an additional 6 g of ethylene glycol was added and the refluxing continued for about an additional sixteen hours. The reaction was cooled and the resulting cloudy solution was cleared by the addition of diethyl ether. The solution was washed with dilute sodium hydroxide and with brine, dried and evaporated to provide 126 g of a pale yellow solid which was recrystallized from about 900 ml of 2:1 hexane:cyclohexane to provide 113 g of yellow crystalline 2-(5-bromo-2-benzyloxyphenyl)-1,3-dioxolane, m.p. 92°–94° C. The infrared spectrum of the product was consistent with the assigned structure.

Part C

Under a nitrogen atmosphere 83.5 g (0.835 mole) of 2,2,2-trifluoroethanol was added dropwise with cooling to a suspension of 16.0 g (0.668 mole) sodium hydride in 90 ml dimethylformamide. The reaction mixture was stirred at about 25° C. for 30 minutes after the addition was complete 9.0 g of copper(II)bromide was added and the reaction was heated to about 105° C. A solution of 112 g (0.334 mole) of 2-(5-bromo-2-benzyloxyphenyl)-1,3-dioxolane in 175 ml dimethylformamide was added dropwise over a period of one and a half hours. The reaction was heated at 105° C. for an additional two hours then diluted with 1.2 liters of cold water and acidified by a slow addition of concentrated hydrochloric acid. The mixture was diluted with 500 ml of ethanol, heated on a steam bath for about one hour and then allowed to stand at 25° C. for about sixteen hours. The reaction mixture was concentrated to remove most of the ethanol then diluted with enough water to bring the total volume to about 2 liters and chilled. The resulting dirty yellow solid was collected, dried in a vacuum oven and then dissolved in chloroform and washed through a Florosil ® column. The eluent was evaporated to provide 102 g of canary yellow solid 2-benzyloxy-5-(2,2,2-trifluoroethoxy)benzaldehyde. The infrared spectrum of this product was consistent with the assigned structure.

Part D

A solution of 27.0 g (0.087 mole) of 2-benzyloxy-5-(2,2,2-trifluoroethoxy)benzaldehyde in 120 ml of ethanol was combined with a solution of 9.1 g (0.13 mole) of hydroxylamine hydrochloride and 10.7 g (0.13 mole) of sodium acetate in 60 ml of water and heated at reflux for about eight hours. The reaction mixture was allowed to stand at about 25° C. for about sixteen hours before being concentrated to remove most of the ethanol. The concentrate was diluted with cold water and chilled. The resulting solid was collected, washed with water and dried to give 28 g of a pale yellow solid. This solid was recrystallized from 250 ml of 3:2 heptane:toluene to provide 23.2 g of pale yellow 2-benzyloxy-5-(2,2,2-trifluoroethoxy)benzaldehyde oxime, m.p. 93°–95° C. Calculated for $C_{16}H_{14}F_3NO_3$: %C, 59.1; %H, 4.3; %N, 4.3; Found: %C, 59.1; %H, 4.2; %N, 4.2.

Part E

To a suspension of 6.0 g (0.073 mole) of sodium acetate in 40 ml of acetic anhydride was added 19.8 g (0.061 mole) of 2-benzyloxy-5-(2,2,2-trifluoroethoxy)benzaldehyde oxime. The resulting mixture was heated at reflux for five hours, cooled and then poured into 400 ml of water. The resulting precipitate was collected, washed with water and dried to provide 18.4 g of a dirty beige solid. This solid was dissolved in chloroform and washed through a Florosil ® column. The eluent was evaporated to provide 18.2 g of an ivory solid which was recrystallized from 3:1 heptane:toluene to provide 16.2 g of white crystalline 2-benzyloxy-5-(2,2,2-trifluoroethoxy)benzonitrile, m.p. 105°–107° C. Calculated for $C_{16}H_{12}F_3NO_2$: %C, 62.5; %H, 3.9; %N, 4.55; Found: %C, 62.6; %H, 3.8; %N, 4.5.

Part F

A mixture containing 3.07 g (0.01 mole) of 2-benzyloxy-5-(2,2,2-trifluoroethoxy)benzonitrile, 0.48 g (0.012 mole) of sodium hydroxide, 15 ml of ethylene glycol and 5 ml of water was refluxed with vigorous stirring for about eighteen hours. The reaction mixture was poured into about 120 ml of water then extracted twice with diethyl ether. The aqueous layer was acidified with concentrated hydrochloric acid and chilled. The resulting precipitate was collected and dried to provide 2.6 g of a white solid which was recrystallized from a mixture of heptane and chloroform to provide 2.2 g of white crystalline 2-benzyloxy-5-(2,2,2-trifluoroethoxy)benzoic acid, m.p. 75°–77° C. Analysis: Calculated for $C_{16}H_{13}F_3O_4$: %C, 58.9; %H, 4.0; Found: %C, 58.7; %H, 3.7.

Part G

To a stirred solution of 16.3 g (0.05 mole) of 2-benzyloxy-5-(2,2,2-trifluoroethoxy)benzoic acid in 80 ml of toluene was added 10.7 g (0.0515 mole) of phosphorous pentachloride. The reaction mixture was stirred at about 25° C. for about two hours and then at about 60° C. for about one and a half hours before being cooled and concentrated to provide 10.7 g of white solid 2-benzyloxy-5-(2,2,2-trifluoroethoxy)benzoyl chloride. The infrared and nuclear magnetic resonance spectra of this product were consistent with the assigned structure.

Part H

A solution of 54.0 g (0.157 mole) of 2-benzyloxy-5-(2,2,2-trifluoroethoxy)benzoyl chloride in 250 ml of benzene was added dropwise with vigorous stirring to a suspension of 18.6 g (0.172 mole) of 2-aminomethylpyridine and 49.8 g (0.47 mole) of sodium carbonate in 400 ml of benzene. After the addition was complete the reaction mixture was heated at reflux for about one hour then cooled and concentrated to remove the benzene. The concentrate was diluted with methylene chloride and water. The layers were separated and the aqueous layer was extracted with methylene chloride. The combined methylene chloride layers were washed once with dilute sodium hydroxide and once with brine, dried and evaporated to provide 62.7 g of a tan solid. This solid was dissolved in chloroform and put through a Florosil ® column. The eluent was evaporated to provide 58.3 g of an ivory powder. A small amount of this powder was recrystallized from 1:1 heptane:toluene to provide white crystalline 2-benzyloxy-N-(2-pyridylmethyl)-5-(2,2,2-trifluoroethoxy)benzamide, m.p. 115°–116° C. Analysis Calculated for $C_{22}H_{19}F_3N_2O_3$: %C, 63.5; %H, 4.6; % N, 6.7; Found: %C, 64.0; %H, 4.7; %N, 6.6.

Part I

Under a nitrogen atmosphere a solution of 56.0 g (0.134 mole) of 2-benzyloxy-N-(2-pyridylmethyl)-5-(2,2,2-trifluoroethoxy)benzamide in 500 ml of acetic acid was added to a paste of 2.5 g of 5% palladium on carbon with acetic acid and hydrogenated on a Parr apparatus. The reaction mixture was filtered to remove catalyst then concentrated to remove the acetic acid. The residue was taken up in methylene chloride, washed once with brine, once with dilute sodium bicarbonate and again with brine, dried and evaporated to provide 33.8 g of a dirty yellow solid. This material was dissolved in a mixture of chloroform and methylene chloride and put through a Florosil ® column. The eluent was evaporated to provide 28.5 g of a pale yellow granular solid. A sample of this material was recrystallized from toluene to provide white crystalline 2-hydroxy-N-(2-pyridylmethyl)-5-(2,2,2-trifluoroethoxy)benzamide, m.p. 143°–145° C. Analysis: Calculated for $C_{15}H_{13}F_3N_2O_3$: %C, 55.2; %H, 4.0; %N, 8.6; Found: %C, 55.3; %H, 4.1; %N, 8.5.

EXAMPLE XXIII

Preparation of 5-Butoxy-2-(2,2,2-trifluoroethoxy)-N-(2-piperidylmethyl)benzamide Acetate

Part A

A mixture containing 59.5 g (0.327 mole) of ethyl 2,5-dihydroxybenzoate. 68.5 g (0.5 mole) butyl bromide and 69 g (0.5 mole) of potassium carbonate in 500 ml of acetone was heated at reflux for about sixteen hours. The reaction mixture was concentrated to remove the acetone then diluted with water and diethyl ether. The layers were separated and the aqueous layer was extracted with diethyl ether. The diethyl ether layers were combined, washed with water, dried and then evaporated to provide 76 g of a mobile brown liquid. This liquid was distilled (103°–107° C./0.1 mm) to provide 67 g of ethyl 5-butoxy-2-hydroxybenzoate.

Part B

To a refluxing mixture of 9.5 g (0.04 mole) of ethyl 5-butoxy-2-hydroxybenzoate and 9.0 g (0.065 mole) of potassium carbonate in 60 ml of acetone was added dropwise 13.9 g (0.06 mole) of 2,2,2-trifluoroethyl trifluoromethanesulfonate. After the addition was complete the reaction was heated at reflux for about sixteen hours. The reaction mixture was cooled, concentrated to remove the acetone and then diluted with water and extracted with diethyl ether. The diethyl ether extract was washed with brine, dried and evaporated to provide 13 g of a clear golden liquid. The structure was confirmed by nuclear magnetic resonance spectroscopy. The liquid was distilled (110°–114° C./0.08 mm) to provide 10.1 g of ethyl 5-butoxy-2-(2,2,2-trifluoroethoxy)benzoate as a clear, colorless liquid.

Part C

A solution of 2.5 g (0.062 mole) of sodium hydroxide in 60 ml of water was combined with 9.9 g (0.031 mole) of ethyl 5-butoxy-2-(2,2,2-trifluoroethoxy)benzoate and 50 ml of ethanol. The reaction mixture was heated at reflux for about sixteen hours then concentrated to remove most of the ethanol, diluted with water and acidified with 10% hydrochloric acid. The resulting solid was collected then recrystallized from a mixture of ethanol and water to provide 7.0 g of white crystalline 5-butoxy-2-(2,2,2-trifluoroethoxy)benzoic acid, m.p. 88.5°–90° C. Analysis: Calculated for $C_{13}H_{15}F_3O_4$: %C, 53.4; %H. 5.2; Found: %C, 53.3; %H, 5.0.

Part D

A mixture of 15.5 g (0.053 mole) of 5-butoxy-2-(2,2,2-trifluoroethoxy)benzoic acid and 11.0 g (0.053 mole) of phosphorous pentachloride was stirred at about 25° C. for about three hours and then concentrated to provide 17.3 g of the acid chloride as a mobile pale yellow liquid. The crude acid chloride was dissolved in 50 ml of benzene and then added dropwise to a vigorously stirred mixture of 22.5 g (0.212 mole) of sodium carbonate and 5.95 g (0.055 mole) of 2-aminomethylpyridine in 100 ml of benzene. The resulting mixture was stirred at about 25° C. for about sixteen hours and then concentrated to remove the benzene. The residue was diluted with methylene chloride and water. The layers were separated and the methylene chloride layer was washed with brine, dried and evaporated to provide 19 g of a lemon yellow solid. The solid was recrystallized from about 230 ml of 2:1 ethanol:water to provide 13.8 g of ivory crystalline 5-butoxy-2-(2,2,2-trifluoroethoxy)-N-(2-pyridylmethyl)benzamide. m.p. 80°–83° C. Analysis: Calculated for $C_{19}H_{21}F_3N_2O_3$: %C, 59.7; %H. 5.55; %N, 7.3; Found: %C. 59.4; %H, 5.4; %N, 7.2.

Part E

Under a nitrogen atmosphere a solution of 8.0 g (0.021 mole) of 5-butoxy-2-(2,2,2-trifluoroethoxy)-N-(2-pyridylmethyl)benzamide in 150 ml of acetic acid was added to a paste of 0.3 g platinum oxide/acetic acid. The resulting mixture was hydrogenated on a Parr apparatus then filtered to remove the catalyst. The filtrate was concentrated to provide a clear, colorless syrup which was triturated with diisopropyl ether. The resulting solid was collected and then recrystallized from about 90 ml of acetonitrile to provide 5.2 g of white solid 5-butoxy-2-(2,2,2,trifluoroethoxy)-N-(2-piperidylmethyl)benzamide acetate, m.p. 127°–129° C. Analysis: Calculated for $C_{19}H_{27}F_3N_2O_3 \cdot C_2H_4O_2$: %C, 56.2; %H, 7.0; %N, 6.25; Found: %C, 56.3; %H, 7.1; %N, 6.1.

EXAMPLE XXIV

Preparation of 5-Ethoxy-2-(2,2,2-trifluoroethoxy)-N-(2-piperidylmethyl)benzamide Acetate

Part A

Using the general method of Example XXIII Part A, 31.2 g (0.20 mole) of ethyl iodide was reacted with 27.3 g (0.15 mole) of ethyl 2,5-dihydroxybenzoate to provide 22 g of white crystalline ethyl 5-ethoxy-2-hydroxybenzoate, m.p. 64°–66° C.

Part B

Using the general method of Example XXIII Part B, 21 g (0.1 mole) of ethyl 5-ethoxy-2-hydroxybenzoate was reacted with 34.8 g (0.15 mole) of 2,2,2-trifluoroethyl trifluoromethanesulfonate to provide 23.6 g of clear colorless liquid ethyl 5-ethoxy-2-(2,2,2-trifluoroethoxy)benzoate b.p. 97°–100° C./0.1 mm. The infrared and nuclear magnetic resonance spectra were consistent with the desired compound.

Part C

Using the general method of Example XXIII Part C, 23 g of ethyl 5-ethoxy-2-(2,2,2-trifluoroethoxy)benzoate was reacted to provide 15.6 g of white solid 5-ethoxy-2-(2,2,2-trifluoroethoxy)benzoic acid. m.p. 101.5°–103° C. Analysis: Calculated for $C_{11}H_{11}F_3O_4$: %C, 50.0; %H, 4.2; Found: %C, 49.9; %H, 4.2.

Part D

Using the general method of Example XXIII Part D, 15.4 g (0.058 mole) of 5-ethoxy-2-(2,2,2-trifluoroethoxy)benzoic acid was converted to the acid chloride and then reacted with 2-aminomethylpyridine to provide 14.4 g of white solid 5-ethoxy-2-(2,2,2-trifluoroethoxy)-N-(2-pyridylmethyl)benzamide, m.p. 111°–113° C. Analysis: Calculated for $C_{17}H_{17}F_3N_2O_3$: %C, 57.6; %H, 4.85; %N, 7.9; Found: %C, 57.9; %H, 4.9; %N, 7.9.

Part E

Using the general method of Example XXIII Part E, 7.1 g (0.02 mole) of 5-ethoxy-2-(2,2,2-trifluoroethoxy)-N-(2-pyridylmethyl)benzamide was hydrogenated to provide 5.3 g of white solid 5-ethoxy-2-(2,2,2-trifluoroethoxy)-N-(2-piperidylmethyl)benzamide acetate, m.p. 151°–152° C. Analysis: Calculated for $C_{17}H_{23}F_3N_2O_3 \cdot C_2H_4O_2$: %C, 54.3; %H, 6.5; %N, 6.65; Found: %C, 54.3; %H, 6.5; %N, 6.5.

EXAMPLE XXV

Preparation of 2-Ethoxy-5-(2,2,2,-trifluoroethoxy)-N-(2-piperidylmethyl)benzamide Acetate

Part A

Using the general method of Example XXIII Part A 48.8 g of ethyl 2,5-dihydroxybenzoate was reacted with benzyl chloride to provide 37.2 g of white solid ethyl 5-benzyloxy-2-hydroxybenzoate. m.p. 70°–72° C. The infrared and nuclear magnetic resonance spectra were consistent with the desired compound.

Part B

Under a nitrogen atmosphere a solution of 5.4 g (0.02 mole) of ethyl 5-benzyloxy-2-hydroxybenzoate in 15 ml of dimethylformamide was added dropwise to a suspension of 0.62 g (0.026 mole) of sodium hydride in 25 ml of dimethylformamide. The resulting mixture was stirred for 30 minutes and then 4.7 g (0.03 mole) of ethyl iodide was added dropwise and the temperature was raised to about 60° C. The resulting mixture was stirred at about 60° C. for about sixteen hours. The reaction mixture was cooled, diluted with water and extracted twice with diethyl ether. The diethyl ether extracts were combined, washed with brine, dried and evaporated to provide 5.9 g of a yellow oil. This oil was distilled (140°–150° C./0.1 mm) to provide 4.5 g of ethyl 5-benzyloxy-2-ethoxybenzoate.

Part C

A solution of 4.3 g (0.014 mole) of ethyl 5-benzyloxy-2-ethoxybenzoate in 100 ml of ethanol was added to a paste of 0.4 g palladium on carbon/ethanol and hydrogenated on a Parr apparatus. The reaction mixture was filtered to remove the catalyst and then concentrated to provide 3.0 g of a yellow liquid which solidified. The crude material was dissolved in chloroform and put through a short column of silica gel. The eluent was evaporated to provide about 3 g of ethyl 2-ethoxy-5-hydroxybenzoate as a soft, waxy solid, m.p. 49°–53° C.

Part D

Using the general method of Example XXIII Part B, 18.5 g (0.088 mole) of ethyl 2-ethoxy-5-hydroxybenzoate was reacted with 2,2,2-trifluoroethyl trifluoromethanesulfonate to provide 18.9 g of ethyl 2-ethoxy-5-(2,2,2-(trifluoroethoxy)benzoate as a clear colorless liquid b.p. 107°–110° C./0.15 mm.

Part E

Using the general method of Example XXIII part C, 18.3 g of ethyl 2-ethoxy-5-(2,2,2-trifluoroethoxy)benzoate was reacted to provide 15.8 g of a white granular solid m.p. 98°–100° C. A small portion was recrystallized from 1:1 ethanol:water to provide white solid 2-ethoxy-5-(2,2,2-trifluoroethoxy)benzoic acid, m.p. 101°–103° C. Analysis: Calculated for $C_{11}H_{11}F_3O_4$: %C, 50.0; %H, 4.2; Found: %C, 49.9; %H, 4.2.

Part F

Using the general method of Example XXIII Part D, 15.4 g (0.058 mole) of 2-ethoxy-5-(2,2,2-trifluoroethoxy)benzoic acid was converted to the acid chloride and then reacted with 2-aminomethylpyridine to provide 14.1 g of crystalline 2-ethoxy-5-(2,2,2-trifluoroethoxy)-N-(2-pyridylmethyl)benzamide, m.p. 110°–111° C. Analysis: Calculated for $C_{17}H_{17}F_3N_2O_3$: %C, 57.6; %H, 4.85; %N, 7.9; Found: %C, 57.1; %H, 4.8; %N, 7.8.

Part G

Using the general method of Example XXIII Part E, 6.4 g (0.018 mole) of 2-ethoxy-5-(2,2,2-trifluoroethoxy)-N-(2-pyridylmethyl)benzamide was hydrogenated to provide 5.3 g of white powdery 2-ethoxy-5-(2,2,2-trifluoroethoxy)-N-(2-piperidylmethyl)benzamide acetate, m.p. 137°–139° C. Analysis: Calculated for $C_{17}H_{23}F_3N_2O_3 \cdot C_2H_4O_2$: %C, 54.3; %H, 6.5; %N, 6.65; Found: %C, 54.4; %H, 6.5; %N. 6.6.

The claimed invention is:

1. A compound of the formula

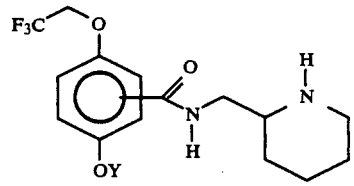

wherein Y is:

straight chain or branched chain alkylene carboxylic acid of 2 to about 6 carbons, or a derivative thereof selected from the group consisting of a primary amide, a secondary lower alkyl amide, a secondary phenyl(lower)alkyl amide, a tertiary amide in which the substituents form a five- or six-membered saturated ring, a tertiary amide wherein the amide substituents are independently lower alkyl, a tertiary amide wherein one amide substituent is lower alkyl and the other is phenyl(lower)alkyl, and a lower alkyl ester; or straight chain or branched chain hydroxyalkyl of 2 to about 6 carbon atoms, or a phenyl ether or lower alkyl ether derivative thereof; or straight chain or branched chain alkenyl of three to about six carbon atoms wherein the olefinic unsaturation does not render the phenolic oxygen vinylic; or straight chain or branched chain phenylalkenyl wherein the alkenyl group contains three to about six carbon atoms and wherein the olefinic unsaturation does not render the phenolic oxygen vinylic;

or a pharmaceutically acceptable acid-addition salt thereof.

2. A compound according to claim 1, of the formula

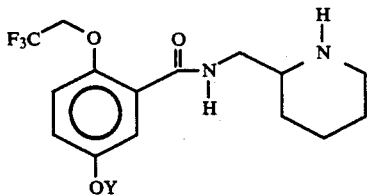

wherein Y is:
  straight chain or branched chain alkylene carboxylic acid of 2 to about 6 carbons, or a derivative thereof selected from the group consisting of a primary amide, a secondary lower alkyl amide, a secondary phenyl(lower)alkyl amide, a tertiary amide in which the substituents form a five- or six-membered saturated ring, a tertiary amide wherein the amide substituents are independently lower alkyl, a tertiary amide wherein one amide substituent is lower alkyl and the other is phenyl(lower)alkyl, and a lower alkyl ester; or
  straight chain or branched chain hydroxyalkyl of 2 to about 6 carbon atoms, or a phenyl ether or lower alkyl ether derivative thereof; or
  straight chain or branched chain alkenyl of three to about six carbon atoms wherein the olefinic unsaturation does not render the phenolic oxygen vinylic;
  straight chain or branched chain phenylalkenyl wherein the alkenyl group contains three to about six carbon atoms and wherein the olefinic unsaturation does not render the phenolic oxygen vinylic;
  or a pharmaceutically acceptable acid-addition salt thereof.

3. A compound according to claim 1, of the formula

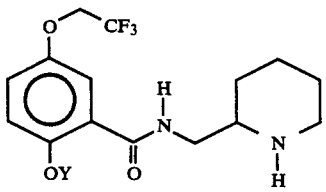

wherein Y is:
  straight chain or branched chain alkylene carboxylic acid of 2 to about 6 carbons, or a derivative thereof selected from the group consisting of a primary amide, a secondary lower alkyl amide, a secondary phenyl(lower)alkyl amide, a tertiary amide in which the substituents form a five- or six-membered saturated ring, a tertiary amide wherein the amide substituents are independently lower alkyl, a tertiary amide wherein one amide substituent is lower alkyl and the other is phenyl(lower) alkyl, and a lower alkyl ester; or
  straight chain or branched chain hydroxyalkyl of 2 to about 6 carbon atoms, or a phenyl ether or lower alkyl ether derivative thereof; or
  straight chain or branched chain alkenyl of three to about six carbon atoms wherein the olefinic unsaturation does not render the phenolic oxygen vinylic;
  straight chain or branched chain phenylalkenyl wherein the alkenyl group contains three to about six carbon atoms and wherein the olefinic unsaturation does not render the phenolic oxygen vinylic;
  or a pharmaceutically acceptable acid-addition salt thereof.

4. A compound according to claim 2 selected from the group consisting of 5-(4-ethoxycarbonylbutoxy)-N-(2-piperidylmethyl)-2-(2,2,2-trifluoroethoxy)benzamide hydrochloride hydrate and 5-(N-isopropylcarbamoylmethoxy)-N-(2-piperidylmethyl)-2-(2,2,2-trifluoroethoxy)benzamide acetate.

5. An antiarrhythmic pharmaceutical composition comprising a compound according to claim 1 and a pharmaceutically acceptable carrier, the compound being present in an amount effective to inhibit or prevent arrhythmia in a mammal.

6. A method for blocking arrhythmia in a mammal, which method comprises administering to the mammal a compound according to claim 1 in an amount effective to inhibit or prevent arrhythmia.

7. The compound 2-benzyloxy-5-(2,2,2-trifluoroethoxy)benzoic acid.

8. A compound of the formula

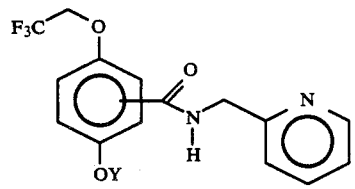

wherein Y is a straight chain or branched chain alkylene carboxylic acid of 2 to about 6 carbon atoms or a derivative thereof selected from the group consisting of a primary amide, a secondary lower alkyl amide, a secondary phenyl(lower)alkyl amide such that the amide nitrogen is not benzylic, a tertiary amide wherein one of the amide substituents is lower alkyl and the other is phenyl(lower)alkyl such that the amide nitrogen is not benzylic, a tertiary amide in which the substituents form a five- or six-membered saturated ring, and a lower alkyl ester; straight chain or branched chain hydroxyalkyl of two to about six carbon atoms, or a phenyl ether or lower alkyl ether derivative thereof.

9. A compound according to claim 8 of the formula

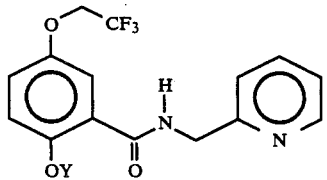

wherein Y is a straight chain or branched chain alkylene carboxylic acid of 2 to about 6 carbon atoms or a derivative thereof selected from the group consisting of a primary amide, a secondary lower alkyl amide, a secondary phenyl(lower) alkyl amide such that the amide nitrogen is not benzylic, a tertiary amide wherein one of the amide substituents is lower alkyl and the other is phenyl(lower)alkyl such that the amide nitrogen is not benzylic, a tertiary amide in which the substituents form a five- or six-membered saturated ring, and a lower alkyl ester; 5 straight chain or branched chain hydroxyalkyl of two to about six carbon atoms, or a phenyl ether or lower alkyl ether derivative thereof.

10. A compound according to claim 8 of the formula

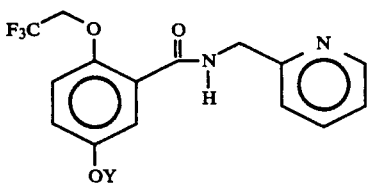

wherein Y is a straight chain or branched chain alkylene carboxylic acid of 2 to about 6 carbon atoms or a derivative thereof selected from the group consisting of primary amide, a secondary lower alkyl amide, a secondary phenyl(lower)alkyl amide such that the amide nitrogen is not benzylic, a tertiary amide wherein one of the amide substituents is lower alkyl and the other is phenyl(lower) such that the amide nitrogen is not benzylic, a alkyl tertiary amide in which the substituents form a five- or six-membered saturated ring, and a lower alkyl ester; straight chain or branched chain hydroxyalkyl of two to about six carbon atoms, or a phenyl ether or lower alkyl ether derivative thereof.

11. The compound 2-hydroxy-N-2-pyridylmethyl)-5-(2,2,2-trifluoroethoxy)benzamide.

12. A compound according to claim 1, wherein Y is a derivative of a straight chain alkylene carboxylic acid of 2 to about 6 carbon atoms, selected from the group consisting of a primary amide, a secondary lower alkyl amide, a secondary phenyl(lower)alkyl amide, a tertiary amide in which the substituents form a five- or six-membered saturated ring, a tertiary amide wherein the amide substituents are independently lower alkyl, a tertiary amide wherein one amide substituent is lower alkyl and the other is phenyl(lower)alkyl.

13. A compound according to claim 3, wherein Y is a derivative of a straight chain hydroxyalkyl containing 2 to about 6 carbon atoms, selected from the group consisting of a phenyl ether and a lower alkyl ether.

14. A compound according to claim 3 selected from the group consisting of
2-(N-Isopropylcarbamoylmethoxy)-N-(2-piperidylmethyl)-5-(2,2,2-trifluoroethoxy)benzamide hydrochloride,
2-(2-methoxyethoxy)-N-(2-piperidylmethyl)-5-(2,2,2-trifluoroethoxy)benzamide acetate,
2-[2-(1-Piperidyloxo)ethoxy]-N-(2-piperidylmethyl)-5-(2,2,2-trifluoroethoxy)benzamide hydrochloride hemihydrate, and
2-(2-hydroxyethoxy)-N-(2-piperidylmethyl)-5-(2,2,2-trifluoroethoxy)benzamide acetate.

15. A compound of the formula

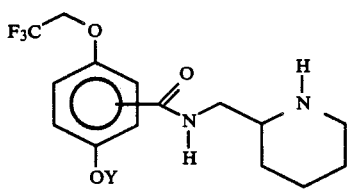

wherein Y is:
ω-phenylalkyl wherein the alkyl group contains one to about three carbon atoms; or
straight chain or branched chain alkyl of 1 to about 6 carbon atoms;
or a pharmaceutically acceptable acid-addition salt thereof.

16. A compound according to claim 15, of the formula

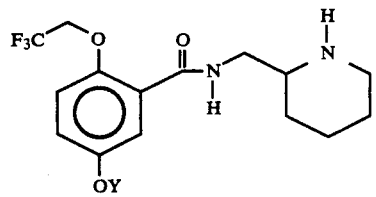

wherein Y is:
ω-phenylalkyl wherein the alkyl group contains one to about three carbon atoms; or
straight chain or branched chain alkyl of 1 to about 6 carbon atoms;
or a pharmaceutically acceptable acid-addition salt thereof.

17. A compound according to claim 15, of the formula

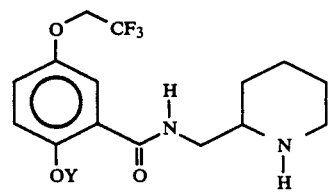

wherein Y is:
ω-phenylalkyl wherein the alkyl group contains one to about three carbon atoms; or
straight chain or branched alkyl of 1 to about 6 carbon atoms;
or a pharmaceutically acceptable acid-addition salt thereof.

18. The compound 2-(3-phenylpropoxy)-N-(2-piperidylmethyl)-5-(2,2,2-trifluoroethoxy)benzamide hydrochloride, according to claim 17.

19. An antiarrhythmic pharmaceutical composition comprising a compound according to claim 15 and a pharmaceutically acceptable carrier, the compound being present in an amount effective to inhibit or prevent arrhythmia in a mammal.

20. A method for blocking arrhythmia in a mammal, which method comprises administering to the mammal a compound according to claim 17 in an amount effective to inhibit or prevent arrhythmia.

21. A compound of the formula

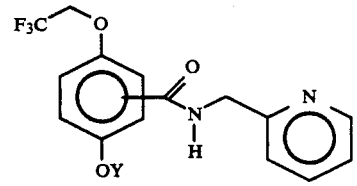

wherein Y is a straight chain or branched chain alkyl of 1 to about 6 carbon atoms.

22. A compound according to claim 21 of the formula
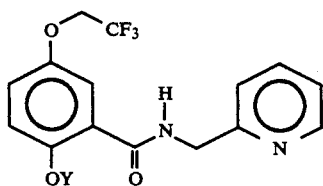
wherein Y is a straight chain or branched chain alkyl of 1 to about 6 carbon atoms.
23. A compound according to claim 21 of the formula
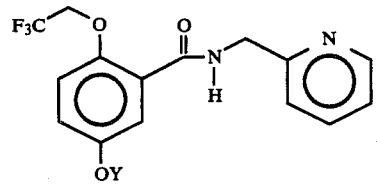
wherein Y is a straight chain or branched chain alkyl of 1 to about 6 carbon atoms.
* * * * *

UNITED STATES PATENT AND TRADEMARK OFFICE
CERTIFICATE OF CORRECTION

PATENT NO.  : 4,952,574
DATED       : August 28, 1990
INVENTOR(S) : Elden H. Banitt It is certified that error appears in the above-identified patent and that said Letters Patent is hereby corrected as shown below:

Col. 23, line 8:   "complete 9.0" should read --complete. 9.0--

Col. 29, line 28:  "vinylic;" should read --vinylic; or--

Col. 29, line 64:  "vinylic;" should read --vinylic; or--

Col. 31, line 15:  "of pri-" should read --of a pri---

Signed and Sealed this

Twelfth Day of May, 1992

Attest:

DOUGLAS B. COMER

Attesting Officer

Acting Commissioner of Patents and Trademarks